US006653505B2

(12) United States Patent
Abbott et al.

(10) Patent No.: US 6,653,505 B2
(45) Date of Patent: Nov. 25, 2003

(54) 3-METHOXYBENZYL THIOUREA DERIVATIVES AND IMPROVED LIPID COMPOSITIONS CONTAINING SAME

(75) Inventors: Thomas P. Abbott, Peoria, IL (US); Alan Wohlman, Northbrook, IL (US)

(73) Assignees: The United States of America as represented by the Secretary of Agriculture, Washington, DC (US); The Fanning Corporation, Chicago, IL (US)

(*) Notice: Subject to any disclaimer, the term of this patent is extended or adjusted under 35 U.S.C. 154(b) by 0 days.

(21) Appl. No.: 09/840,768

(22) Filed: Apr. 23, 2001

(65) Prior Publication Data

US 2001/0056205 A1 Dec. 27, 2001

Related U.S. Application Data

(60) Provisional application No. 60/202,562, filed on May 10, 2000.

(51) Int. Cl.$^7$ ............................................. C07C 335/00
(52) U.S. Cl. .......................................... 564/26; 564/17
(58) Field of Search ..................................... 564/26, 17

(56) References Cited

U.S. PATENT DOCUMENTS

| 2,154,341 A | 4/1939 | Martin et al. ................... 37/16 |
| 2,662,096 A | 12/1953 | Huebner et al. ............. 260/552 |
| 3,483,296 A | 12/1969 | Martin et al. ............... 424/322 |

(List continued on next page.)

FOREIGN PATENT DOCUMENTS

| DE | 208 298 A | 5/1984 |
| EP | 0 466 639 B1 | 6/1991 |
| EP | 0 903 349 A2 | 3/1999 |
| WO | WO 96/28008 | 9/1996 |

OTHER PUBLICATIONS

T.S. Chao et al. "Some Synergistic Antioxidants for Synthetic Lubricants," Symposium on Synthetic and Petroleum–Based Lubricants Presented Before the Division of Petroleum Chemistry, Inc., 27(2), 362–379, American Chemical Society, Las Vegas Meeting, Mar. 28–Apr. 2, 1982.

T.P. Abbott "Oxidative Stability System in Meadowfoam," Abstract from the 89$^{th}$ AOCS Annual Meeting & Expo, Chicago, Illinois, May 10–13, (1998).

M. Rechcigl, Jr. CRC Handbook of Naturally Occuring Food Toxicants, CEC Press, Inc. (Boca Raton, Florida), pp. 15–30 (1983).

S. Vaughn et al. "Isolation and Identification of (3–Methoxyphenyl) Acetonitrile as a Phytotoxin from Meadowfoam (limnanthes alba) Seedmeal," Journal of Chemical Ecology, vol. 22, No. 10, 1939–1949 (1996).

T. Johns et al. "Anti–Reproductive and Other Medicinal Effects of *Tropaeolum Tuberosum*," Journal of Ethnopharmacology 5, 149–161 (1982).

T.A. Isbell et al. "Oxidative Stability Index of Vegetable Oils in Binary Mixtures with Meadowfoam Oil," Industrial Crops and Products 9, 115–123 (1999).

K. Tian et al. "Determination of Oxidative Stability of Oils and Fats," Anal. Chem. 71, 1692–1698 (1999).

S. El. Migirab et al. "Isothiocyanates, Thioureas et Thiocarbamates Isoles De Pentadip landra Brazzeana," Phytochemistry 16, 1719–1721 (1977).

W.W. Christie "Antioxidants," Bell & Bain Ltd., Glasgow, The Oily Press, Ltd. (Dundee, Scotland, 1988), pp. 133–159.

G. Kajimoto et al. "Changes in Organic Acid Formulation in Volatile Degradation Products During Oxidation of Oils Treated with Antioxidant," Fac. Nutr., Kobe Gakuin Univ., Kobe, Japan. Nippon Eiyo, Shokuryo Gakkaishi 51(4), 207–212 (1998), K. Ziegler–Skylakakis "S–Oxygenation of Thiourea Results in the Formation of Genotoxic Products," Environ. Mol. Mutagen. 31(4), 362–373 (1998).

S.L. Mali et al. "Phytochemical Oxidation of Phenyl–3–(2–Pyridyl)Thiourea by Singlet Oxygen," Asian J. Chem. 5(4), 808–812 (1993).

A. Mustafa et al. "Reaction of Thiourea with Hydrogen Peroxide: Carbon–13 NMR Studies of an Oxidative/Reductive Bleaching Process," Text. Res. J. 62(2), 94–100 (1992).

Internet "Uses of Meadowfoam Seed Oil™," Mar. 9, 2000, http://www.meadowfoam.com/uses/htm.

U.S. patent application Ser. No. 09/725,560, Wohlman, filed Nov. 29, 2000.

89$^{th}$ Am. Oil Chem. Soc., May 10–13, 1998, Chicago, Illinois. This presentation discussed some of the compounds that are present in crude meadowfoam seed oil that do not contribute substantially to the oxidative stability of lipids or oils. It did not discuss any 1–(3–methoxybenzyl)–3–substituted thiourea compounds.

Assoc. for the Adv. of Ind. Crops, Oct. 15–17, 2000, St. Louis, MO. This presentation identified the presence of 1,3–di(3–methoxybenzyl) thiourea in meadowfoam seed oil. No other 1–(3–methoxybenzyl)–3–substituted thiourea compounds were discussed.

Martin G. Ettlinger et al. "The Mustard Oil of *Limnanthes douglasii* Seed, m–Methoxybenzyl Isothiocynate," Journal of the American Chemical Society,vol. 78, No. 9, pp. 1952–1954 (1956).

Primary Examiner—Samuel Barts
Assistant Examiner—Elvis O. Price
(74) Attorney, Agent, or Firm—Roberta L. Hastreiter; Scott B. Feder; Lord, Bissell & Brook

(57) ABSTRACT

1-(3-methoxybenzyl)-3-substituted thiourea antioxidant compounds and improved lipids compositions which are supplemented with amounts of such antioxidant compounds effective for augmenting oxidative stability of the base lipid are provided. Also provided are methods for enhancing the oxidative stability of a lipid comprising supplementing a base lipid in need of enhanced oxidative stability with at least one 1-(3-methoxybenzyl)-3-substituted thiourea compound of the present invention.

2 Claims, No Drawings

U.S. PATENT DOCUMENTS

| | | | |
|---|---|---|---|
| 3,743,736 A | 7/1973 | Porter et al. | 424/267 |
| 3,852,348 A | 12/1974 | Teach | 260/553 |
| 3,949,089 A * | 4/1976 | Maxwell et al. | 424/326 |
| 3,991,008 A | 11/1976 | Temin et al. | 260/42.15 |
| 4,925,581 A | 5/1990 | Erickson et al. | 252/48.2 |
| 5,079,304 A | 1/1992 | DeMarco | 525/329.8 |
| 5,262,072 A | 11/1993 | Camenzind et al. | 252/32.7 |
| 5,434,283 A | 7/1995 | Wong et al. | 554/224 |
| 5,441,984 A | 8/1995 | Heath, Jr. et al. | 514/595 |
| 5,747,528 A | 5/1998 | Trivedi | 514/456 |
| 6,013,818 A | 1/2000 | O'Lenick, Jr. | 554/224 |
| 6,136,330 A | 10/2000 | Soliman et al. | 424/401 |
| 6,180,668 B1 | 1/2001 | O'Lenick, Jr. et al. | 514/547 |

\* cited by examiner

3-METHOXYBENZYL THIOUREA DERIVATIVES AND IMPROVED LIPID COMPOSITIONS CONTAINING SAME

CROSS-REFERENCE TO RELATED APPLICATIONS

This application claims the benefit of prior Provisional Application No. 60/202,562, filed on May 10, 2000.

FIELD OF THE INVENTION

This invention relates to novel 1-(3-methoxybenzyl)-3-substituted thiourea compounds and lipid and oil compositions supplemented with such compounds having enhanced oxidative stability.

BACKGROUND OF THE INVENTION

Natural lipids and oils are used in pharmaceutical preparations, food products, cosmetics, and various industrial products such as lubricants, coatings, inks, paints, plastics and the like. Such lipids are subject to oxidative degradation which can affect color, odor, viscosity, and lubricity characteristics thereof, adversely affecting the quality of the commercial products containing such lipids. In the food, cosmetics and pharmaceutical industries, maintaining high quality color and odor of oils and other lipids is important to avoiding oxidation-induced rancidity which is affected by factors such as the oxygen concentration, light and heat, as well as the degree of unsaturation of the lipid or oil, and the amount of natural or synthetic antioxidants present therein. Biodegradable lipids, oils and derivatives thereof used as cutting lubricants are recognized to be adversely affected by heat induced oxidation.

Meadowfoam (*Limnanthes alba*) seed oil has been demonstrated to be highly stable to oxidation. Although the identity of the compound(s) responsible for exceptional oxidative stability of meadowfoam oil is heretofore unknown, mixing meadowfoam oil with other oils imparts enhanced oxidative stability to the mixture. (Isbell, T. A., Abbott, T. A. and Carlson, K. D. 1999. Ind. Crops Prod. 9(2):115–123). Several minor constituents in meadowfoam oil which either diminish oxidative stability or impart small increases in oxidative stability of meadowfoam oil are known, however. (Abbott, T. P. and Isbell, T. A. 1998. Abstracts of the 89th American Oil Chemist's Society Annual Meeting & Expo, Chicago, Ill., May 10–13, 1998. p 66). Refined meadowfoam oil (and other refined seed oils and vegetable oils) exhibit reduced oxidative stability as a result of the refining process. Meadowfoam is known to contain 3-methoxyphenyl acetonitrile, 3-methoxybenzyl isothiocyanate and 3-methoxybenzaldehyde. When added to refined meadowfoam oil at levels from about 0.1% to 1.0%, these compounds exhibit only small to moderate antioxidative effects, at best.

Thiourea has been shown to possess antioxidative activity in oils (Kajimoto and Murakami Nippon Eiyo, Shokuryo Gakkaishi 51(4):207–212, 1998; Chemical Abstract 129:188538); but thiourea is not very soluble in oils. The oxidative stability of ester-based synthetic lubricants (i.e., not vegetable oils) stabilized with amine antioxidants has been shown to be enhanced with specific thioureas (Chao and Kjonaas Amer. Chem. Soc. Preprints, Div. Pet. Chem. 27(2):362–379, 1982). Camenzind and Rolf, Eur. Pat. Appl. EP 91–810474, Chemical Abstract 117:30273, show that certain acylated thioureas are able to increase the oxidative stability to lubricants and hydraulic fluids.

Mono- and di-substituted thiourea compounds also have been described in U.S. Pat. Nos. 2,154,341, 2,662,096, 3,852,348, and 3,991,008. Migirab et al. *Phytochem.* 16(11):1719–1721, (1977) disclose methoxy-substituted aromatic thioureas such as N,N'-bis[(4-methoxyphenyl)methyl]-thiourea (CAS #22313–70–8), which is isolated from P. brazzeana.

There is a need for antioxidant compounds and compositions, especially natural antioxidants or derivatives thereof, that are soluble in lipids and oils and are capable of imparting oxidative stability thereto when added at low concentrations.

SUMMARY OF THE INVENTION

We have now unexpectedly discovered that excellent oxidative stability may be imparted to lipids and oils by compounds of the formula I,

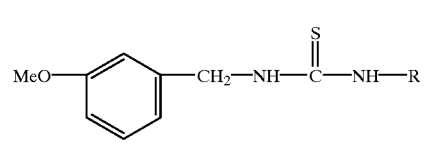

wherein R is a $C_1$–$C_{20}$ linear or branched alkyl such as methyl, ethyl, propyl, isopropyl, butyl, isobutyl, tert-butyl, pentyl, hexyl, octyl, decyl, nonyl, dodecyl, and the like, $C_5$–$C_7$ cycloalkyl, such as cyclopentyl, cyclohexyl or cycloheptyl and the like, $C_6$–$C_7$ aryl such as phenyl or benzyl and the like, hydroxy- or alkoxy-substituted $C_6$–$C_7$ aryl such as hydroxyphenyl, methoxyphenyl, ethoxyphenyl, hydroxybenzyl, methoxybenzyl, ethoxybenzyl. Among compounds of the formula I, a presently preferred compound is 1,3-di(3-methoxybenzyl) thiourea, that is a compound of such formula I where R is a 3-methoxybenzyl moiety. An amount of a compound of formula I sufficient to impart oxidative stability to a lipid or oil (or compositions containing such lipids or oils) is from about 0.01 wt. % to about 5.0 wt. % based on the total weight of the lipid or oil.

The present invention also provides oxidatively stable lipid compositions comprising from about 95 wt. % to about 99.99 wt. % of a base lipid or oil and between about 0.01 wt. % and about 5.0 wt. %, more preferably between about 0.05 wt. % and 2.0 wt. %, and most preferably between about 0.1 wt. % and 1.0 wt. % of a compound of formula I. Lipids or oils of the present invention containing between about 3 wt. % and about 5 wt. % or more of a substituted thiourea compound of formula I, based on the total weight of the base lipid or oil composition, may be used as "concentrates" and conveniently added to processed seed oils or other lipids in need of enhanced oxidative stability to provide a lipid or oil composition of the present invention.

The present invention further provides a method for imparting oxidative stability to a base lipid or oil composition in need of enhanced oxidative stability, comprising the step of supplementing a base lipid or oil with an amount of a compound of formula I sufficient to impart enhanced oxidative stability to the base lipid or oil.

Presently preferred compounds of formula I are 1,3-di(3-methoxybenzyl) thiourea; 1-(3-methoxybenzyl)-3-ethyl-2-thiourea; 1-(3-methoxybenzyl)-3-propyl-2-thiourea; 1-(3-methoxybenzyl)-3-hexyl-2-thiourea; 1-(3-methoxybenzyl)-3-dodecyl-2-thiourea; 1-(3-methoxybenzyl)-3-(4-hydroxyphenyl)-2-thiourea; and 1-(3-methoxybenzyl)-3-(3-methoxyphenyl)-2-thiourea. 1,3-di(3-methoxybenzyl) thiourea, which the inventors have identified as a significant natural antioxidant in meadowfoam seed oil, is a particularly preferred compound of the invention.

It also has been surprisingly found that compounds of formula I, in combination with a benzylamine compound such as N-substituted benzylamines, exhibit a synergistic oxidative stabilizing effect in lipids and oils. Various naturally occurring lipids and oils, such as seed oils and vegetable oils contain benzylamine compounds. In these cases, the synergistic effect may be obtained by supplementing such a base lipid or oil with a compound of formula I and, optionally, with an exogenously added benzylamine compound in an amount sufficient to impart yet a further enhancement in oxidative stability. Thus, another aspect of the present invention entails lipid compositions comprising (i) a compound of Formula I and (ii) a benzylamine or N-substituted benzylamine compound to impart enhanced oxidative stability.

DETAILED DESCRIPTION OF THE INVENTION

In one of its aspects, the present invention entails 1-(3-methoxybenzyl)-3-substituted thiourea compounds of the formula:

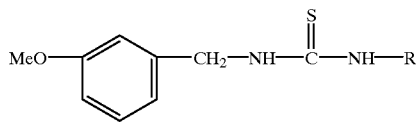

wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl. In a particularly preferred embodiment, the substituted aryl moiety is a 3-hydroxy-substituted or 3-alkoxy-substituted aryl compound.

In another of its aspects, the present invention entails a lipid composition with enhanced oxidative stability comprising from about 95 wt. % to about 99.99 wt. % of a base lipid and from about 0.01 wt. % to about 5.0 wt. %, more preferably between about 0.05 wt. % and 2.0 wt. %, and still more preferably about 0.1 wt. % to about 1.0 wt. % of a 1-(3-methoxybenzyl)-3-substituted thiourea compound of the formula:

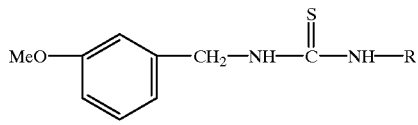

wherein R is selected from the group consisting of $C_1$–$C_{20}$ linear or branched alkyl; C5–$C_7$ cycloalkyl; hydroxy- or alkoxy-substituted $C_5$–$C_7$ cycloalkyl; $C_6$–$C_7$ aryl; and hydroxy- or alkoxy-substituted $C_6$–$C_7$ aryl.

In a further of its aspects, the present invention entails a method of enhancing the oxidative stability of a lipid, comprising the step of combining a lipid with an oxidative stability-enhancing amount of a compound of the formula I:

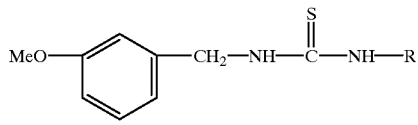

wherein R is selected from the group consisting of $C_1$–$C_{20}$ linear or branched alkyl; $C_5$–$C_7$ cycloalkyl; hydroxy- or alkoxy-substituted $C_5$–$C_7$ cycloalkyl; $C_6$–$C_7$ aryl; and hydroxy- or alkoxy-substituted $C_6$–$C_7$ aryl.

The compounds of the present invention may be added to essentially any lipid in which the compounds of the invention are soluble to augment the oxidative stability of such lipid. The term "lipid" as used herein includes vegetable oils, seed oils, triglycerides, waxes of triglycerides, and phospholipids. Among the lipids that may be supplemented with amounts of the compounds of the present invention to impart enhanced oxidative stability are vegetable oil, peanut oil, corn oil, cottonseed oil, safflower oil, soybean oil, rapeseed (canola) oil, palm oil, and olive oil, jojoba wax ester, and lecithin. As used herein, the phrase "base lipid", "base oil" or equivalent phrase means a lipid or oil to which a compound of formula I has not been exogenously added.

As used herein, "$C_1$–$C_{20}$ linear or branched alkyl" shall include methyl, ethyl, propyl, isopropyl, butyl, isobutyl, t-butyl, pentyl, 2-methyl-pentyl, 3-methyl-penyl, hexyl, octyl, decyl, dodecyl, and the like. The term "$C_5$–$C_7$ cycloalkyl" shall include cyclopentyl, cyclohexyl and cycloheptyl. The term "hydroxy- or alkoxy-substituted $C_5$–$C_7$ cycloalkyl" shall include cyclopentyl, cyclohexyl and cycloheptyl moieties that are substituted with an hydroxy, methoxy, ethoxy, or propoxy group or the like. The term "$C_6$–$C_7$ aryl" shall include phenyl and benzyl. The term "hydroxy- or alkoxy-substituted $C_6$–$C_7$ aryl" shall include phenyl and benzyl moieties that are substituted with an hydroxy, methoxy, ethoxy, or propoxy group or the like.

By use of the phrase "enhanced oxidative stability", "augmented oxidative stability" or an equivalent phrase, it is meant that a lipid composition of the invention has an increased ability to inhibit oxidation as measure by the Oxidative Stability Index (OSI) disclosed herein, as compared to the base lipid or oil (i.e., one not supplemented with an exogenously added compound of formula I). It is presently preferred that a lipid or oil composition of the invention exhibit an OSI value at least 10% greater, more preferably at least 100% greater, and most preferably at least about 200% greater or more than the OSI value of the base lipid or base oil composition to which it is compared, when the OSI test is carried out at a temperature between about 110° C. and about 130° C.

Compounds of the formula I may be synthesized by reacting 3-methoxybenzylamine and an appropriately selected isothiocyanate compound of the Formula II S=C=N—R, wherein R is defined the same as for compounds of Formula I. The reaction may be carried out by slowly adding the isothiocyanate to an aqueous solution of 3-methoxybenzylamine, preferably under a nitrogen atmosphere. The thiourea product of the reaction, which is a compound of formula I, may be recovered and purified by mixing the reaction products with a solvent that is not miscible with water but one that is a solvent for the thiourea, such as methylene chloride, chloroform, toluene or diethyl ether. The water layer may or may not be acidified to enhance separation and recovery of the thiourea compound of the invention. The thiourea, dissolved in the solvent layer, can be drawn off from the water layer, dried and the resulting crude thiourea purified by recrystallization in an appropriate solvent such as ethanol. See, Example 1. See also, generally, the procedure of Moore and Crossley, Organic Synthesis 2, 617–618 (note 4).

The reactants, 3-methoxybenzylamine and an appropriate isothiocyanate compound as defined above, may be obtained commercially or synthesized by routine methods known in the art, and the resultant product compounds of formula I may be readily isolated by routine methods well-known to those having ordinary skill in the art. Suitable isothiocyanate reactants for synthesizing compounds of the present invention may be obtained as well-known in the art from degradation of glucosinolates present in seed oils and other lipids. In an aqueous solution containing the enzyme thioglucosidase, glucosinolate compounds are degraded into isothiocyanates and other degradation products. See, Vaughn, et al., J. Chem. Ecol. 22, 1939–49 (1996); and C. VanEtten and H. Tookey, (1983) Glucosinolates, pp. 15–30 in M. Rechcigl (ed.) "Naturally Occurring Food Toxicants," CRC Press, Boca Raton, Fla. The isothiocyanate fraction of the glucosinolate breakdown products thus may be isolated and reacted with 3-methoxybenzylamine as described above to provide compounds of the present invention. Approximately 100 glucosinolate compounds have been identified in plants from 11 different plant families including mustard, rapeseed, cabbage, garlic mustard and crambe (S. F. Vaughn, 1999. Glucosinolates as Natural Pesticides in Biologically Active Natural Products: Agrochemicals, H. G. Cutler and S. J. Cutler, Eds, CRC Press, Boac Raton, Fla.) Oils isolated from glucosinolate containing plants are normally deodorized by steam sparging to remove volatile compounds which includes isothiocyanates and amines. Thus, a variety of isothiocyanate compounds and benzylamine compounds may be obtained from the waste distillation product generated in the process of purifying such oils and employed as reactants in synthesizing compounds of the present invention.

3-methoxybenzylamine may be purchased commercially or may be isolated from meadowfoam oil by extraction into an immiscible acidified aqueous layer which is separated from the oil, washed with a nonpolar solvent, treated with a base to lower pH, and the amine extracted into an immiscible solvent. The 3-methoxybenzylamine compound may be further purified by crystallization from ethanol or similar solvent and/or purified by reverse-phase HPLC using a C18 column, eluting with a gradient starting at 100% methanol and proceeding to about 80% methanol: 20% chloroform. The peak containing 3-methoxybenzylamine may be identified by its retention time on the HPLC column in comparison to the retention time for a known standard sample of 3-methoxybenzylamine. Other natural amines may be purchased commercially or may be similarly extracted from natural sources and purified with reference to known standard samples and/or identified by standard chemical methods for identification of amines (e.g., chromatography, infrared spectroscopy, mass spectroscopy, elemental analysis, nuclear magnetic resonance analysis and the like).

The oxidative stability of a lipid, with and without addition of a compound of the present invention, may be determined by procedures that are described in the literature. See, for example, K. Tian and P. Dasgupta, Anal. Chem. 71, 1692–98 (1999). A presently preferred method of determining oxidative stability of lipids and oils employs the oxidative stability index (OSI), which determines the oxidative stability of an oil by passing air through a sample under stringent temperature control. (Firestone, Oxidative Stability Index (OSI): Official Methods of Recommended Practices of the American Oil Chemists' Society, 4$^{th}$ Ed. American Oil Chemists Society, Champaign IL Cd 126–92.). In this method, a stream of air is passed through the oil sample, which aids in the rapid degradation of the triglyceride into volatile organic acids. The air stream flushes the volatile acids from the oil into a conductivity cell containing water where the acids are solubilized. These acids, once dissolved in the water solution, disassociate into ions, thus changing the conductivity of the water. Therefore, a continuous measure of the conductivity of the cell by computer will indicate when a rapid rise in the conductivity occurs that corresponds to the induction point, oxidative failure of the sample. The time to the induction point is the OSI time. An AOCS standard method has been recently developed and a collaborative study has also been published (Jebe et al., J. Am. Oil Chem. Soc. 70, 1055–61 (1993)), demonstrating that the OSI method has good reproducibility among samples and laboratories. Saturated fatty acid methyl ester (FAME) standards commercially available from Alltech Associates (Deerfield, Ill.) may be used to calibrate the OSI determinations.

OSI determinations may be performed on a oxidative stability instrument manufactured by Omnion (Rockland, Mass.) using the AOCS method described in the above-disclosed Firestone reference. Lipid or oil samples may be run at 110° C. and FAMEs may be tested at 90° C., with air flow set at 35 kPa with a resulting velocity of about 140 ml/min. A presently preferred method for determining OSI values is described by T. A. Isbell et al., Industrial Crops and Products 9, 115–123 (1999).

Compounds of the formula I may be conventionally mixed with a suitable lipid or oil and solubilized at concentrations up to 3.0%–5.0% or more. It is presently contemplated that concentrations of a compound of formula I between about 0.1% and 1.0% are sufficient to provide up to about 2-fold to 10-fold enhancement in oxidative stability of a base lipid or oil in need of enhanced oxidative stability. However, lipids or oils of the present invention containing up to 3.0%–5.0% of a compound of formula I are useful as "concentrates" that can be conveniently diluted up to 30- to 50-fold or more with a base lipid in need of enhanced oxidative stability. The base composition of such a concentrate may itself be a lipid or oil such as a seed oil or vegetable oil or a food grade solvent. Moreover, a compound of formula I, optionally in combination with an amine compound, such as 3-methoxybenzylamine, may be provided in an oil-in-water emulsion or a water-in-oil emulsion, or the like. The emulsions are presently contemplated to be especially useful as additives to biodegradable cutting lubricants such as canola oil, soybean oil, vegetable oil estolyte, or other cutting lubricants to enhance the oxidative stability of such lubricants.

In presently preferred embodiments of the lipid or oil compositions of the invention, the base lipid or oil is supplemented with an effective amount of a compound of formula I, e.g., a concentration of between about 0.1% and 1.0%, as well as a benzylamine compound present in an amount sufficient to augment the oxidative stability imparted by the compound of formula I. The amount of a benzylamine compound to be added to a lipid or oil composition of the invention may be determined by observing increases in OSI values as a function of amount of the benzylamine compound added. While a base lipid or oil may inherently contain an amine compound, additional amounts of an amine compound, preferably 3-methoxybenzylamine, may be added to a lipid or oil that has been supplemented with a compound of formula I to increase the oxidative stability of such a lipid or oil composition of the present invention. The amount of such an amine compound to be added to a lipid or oil composition of the invention to achieve a synergistic anti-oxidation effect may be determined empirically by adding predetermined amounts of the amine compound to aliquots of the lipid or oil composition containing a compound of formula I and measuring the increase in OSI value obtained.

The following nonlimiting examples further describe the preparation of the compounds of the invention. Unless otherwise stated, all percentages are weight percentages (wt. %).

EXAMPLE 1

This example demonstrates the synthesis of 1,3-di(3-methoxybenzyl) thiourea. To a three neck, 100 ml flask fitted with a condenser, a rubber syringe septum and a nitrogen inlet was added 20 ml water and 3.6 g (25.8 mmol) of 3-methoxybenzyl amine. The reaction vessel was purged with nitrogen and stirred with a teflon-coated magnetic stir bar. 3-Methoxybenzyl isothiocyanate 2.59 ml (3.0 g, 16.7 mmol) was added dropwise (~1 drop/5–10 s) from a glass syringe. A separate layer forms and the mixture was stirred for 1 h at room temperature. The water layer was acidified with 1 M HCl (about 10 ml) to pH 5.5. Methylene chloride (15 ml) was added and the two layers transferred to a separator funnel. The lower layer (methylene chloride) was removed. The water layer was washed with methylene chloride, twice more with 10 ml methylene chloride, and the combined $CHCl_2$ solutions were washed with 0.1 M HCl and then water. The $CHCl_2$ solution was dried over 3A molecular sieves and then evaporated to dryness in a rotating solvent evaporator. The resulting viscous liquid was taken up in 20 ml ethanol that had been heated to 35° C. and the product recrystallized by cooling in a refrigerator twice from ethanol as white crystals, dried in vacuum at room temperature and weighed. A second recrystallization was made from the mother liquor to retrieve additional product for a yield of 79.8% in the first crystal batch and 83.2% for the combined batches of crystals. Analysis of the product by NMR, mass spectroscopy and elemental analysis revealed the product to be 1,3-di(3-methoxybenzyl) thiourea.

EXAMPLE 2

Jojoba oil (extracted from jojoba seed with hexane) is a wax ester with monounsaturated C20 and C22 acids and alcohols esterified together. Jojoba oil (20 g) was mixed with 20 mg (0.1%) of the 1,3-di(3-methoxybenzyl) thiourea prepared in Example 1. An Oxidative Stability test at 110° C. on 5 g samples of the mixture (in triplicate) revealed an OSI time of 64.2 h, a 30% improvement compared to an OSI time of 49.2 h for the jojoba oil alone. OSI time is the time for oxygen bubbling through the oil at a constant rate to break the oil down and generate detectable oxidation products. When the 1,3-di(3-methoxybenzyl) thiourea product from Example 1 was added at the 1% level, OSI time increased to 168 h, a 241% improvement as compared to jojoba oil alone.

EXAMPLE 3

Refined meadowfoam oil is a highly monounsaturated vegetable oil whose oxidative stability is reduced in refining processes. Meadowfoam oil (20 g, Lot #C-9773, The Fanning Corp) was mixed with 20 mg (0.1%) of the 1,3-di(3-methoxybenzyl) thiourea prepared in Example 1. An Oxidative Stability test at 110° C. on 5 g samples of the mixture (in triplicate) revealed an OSI time of 76.4 h, a 15% improvement compared to an OSI time of 66.3 h for the meadowfoam oil alone. When the 1,3-di(3-methoxybenzyl) thiourea product from Example 1 was added at the 1% level, OSI time increased to 211 h, a 218% improvement.

EXAMPLE 4

The 1,3-di(3-methoxybenzyl) thiourea prepared in Example 1 was mixed at 0.1%, 0.5% or 1.0% with refined meadowfoam oil (Lot #CW-4551, The Fanning Corp) and the oxidative stability of the mixtures compared to that of refined meadowfoam oil at 130° C. The OSI times were 49.8 h, 159 h and 172 h respectively for the mixtures containing the thiourea compared to an OSI time of 14.9 h for this lot of refined meadowfoam oil with no additives at 130° C. Accordingly, supplementing the refined meadowfoam oil with 0.1%, 0.5%, and 1.0% 1,3-di-3-methoxybenzyl thiourea provided increases in the OSI time of 234%, 967%, and 1054%, respectively.

EXAMPLE 5

High oleic sunflower oil is a highly monounsaturated vegetable oil. High oleic sunflower oil (20 g, Florasun Brand, Floratech, Gilbert, Ariz.) was mixed with 200 mg (1.0%) of the 1,3-di(3-methoxybenzyl) thiourea prepared in Example 1. An Oxidative Stability test at 130° C. on 5 g samples of the mixture (in triplicate) revealed an OSI time of 157 h, a 1720% improvement compared to an OSI time of 9.13 h for the sunflower oil alone.

EXAMPLE 6

Disubstituted thioureas available commercially that do not have a 3-methoxybenzyl moiety have lower antioxidant protection for monounsaturated oils. Thus, 1,3-bis(2-methoxyphenyl)-2-thiourea (Aldrich Chem Co.) added at 0.1% to refined meadowfoam oil gave an OSI time of 37.1 h at 130° C., a 34% lower value than for the thiourea produced in Example 1. Likewise, 1,3-bis(3-methoxyphenyl)-2-thiourea at 0.1% added to refined meadowfoam oil gave an OSI time of 27.0 h, an 84% lower value than for the thiourea produced in Example 1.

EXAMPLE 7

Soybean oil is a highly polyunsaturated vegetable oil. Soybean oil (20 g) was mixed with 200 mg (1.0%) of the 1,3-di(3-methoxybenzyl) thiourea prepared in Example 1. An Oxidative Stability test at 130° C. on 5 g samples of the mixture (in triplicate) revealed an OSI time of 6.4 h, an 831% improvement compared to an OSI time of 0.77 h for the soybean oil alone.

EXAMPLE 8

Milkweed seed oil is a highly polyunsaturated vegetable oil. Milkweed seed oil (20 g, extracted from the seed with hexane) was mixed with 200 mg (1.0%) of the thiourea prepared in Example 1. An Oxidative Stability test at 130° C. on 5 g samples of the mixture (in triplicate) revealed an OSI time of 2.78 h, an 654% improvement compared to an OSI time of 0.42 h for the milkweed oil alone.

EXAMPLE 9

Analysis of crude and refined meadowfoam oil by high performance liquid chromatography (hplc) gave a peak at retention time 9.5 minutes in the crude but not the refined oil. The retention time for the compound synthesized in Example 1, above, was 9.575 to 9.613 in different concentrations. Also, an extract of crude meadowfoam oil with acetonitrile solvent was separated into its components by hplc and one component was identified by mass spectroscopy, NMR and elemental analysis to be 1,3-di(3-methoxybenzyl) urea, an oxidized form of the thiourea synthesized in claim 1. Accordingly, 1,3-di(3-methoxybenzyl) thiourea is shown to be a natural component in crude meadowfoam oil when extracted from the seed and not refined.

We claim:

1. A compound of the formula:

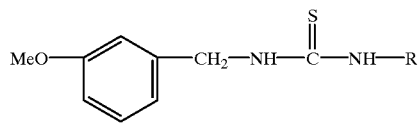

wherein R is a $C_5$–$C_7$ cycloalkyl, an alkoxy-substituted $C_5$–$C_7$ cycloalkyl or a hydroxy-substituted $C_5$–$C_7$ cycloalky.

2. A compound of claim 1 wherein R is cyclopentyl, cyclohexyl or cycloheptyl.

* * * * *

UNITED STATES PATENT AND TRADEMARK OFFICE
CERTIFICATE OF CORRECTION

PATENT NO. : 6,653,505 B2
DATED : November 25, 2003
INVENTOR(S) : Thomas P. Abbott and Alan Wohlman It is certified that error appears in the above-identified patent and that said Letters Patent is hereby corrected as shown below:

Column 3,
Line 52, change "$C5-C_7$" to -- $C_5 - C_7$ --.

Column 8,
Line 63, change "cycloalky" to -- cycloalkyl --.

Signed and Sealed this

Twenty-fifth Day of January, 2005

JON W. DUDAS
*Director of the United States Patent and Trademark Office*